United States Patent [19]

Krogh

[11] Patent Number: 4,622,413
[45] Date of Patent: Nov. 11, 1986

[54] METHOD FOR PREPARING AMINO ACID ESTER HYDROHALIDES

[75] Inventor: James A. Krogh, Mount Prospect, Ill.

[73] Assignee: PPG Industries, Inc., Pittsburgh, Pa.

[21] Appl. No.: 645,894

[22] Filed: Aug. 31, 1984

[51] Int. Cl.$^4$ ............................................. C07C 67/08
[52] U.S. Cl. ..................... 560/38; 546/335; 548/344; 548/491; 548/532; 548/535; 560/40; 560/153; 560/155; 560/168; 560/169; 560/170; 560/171; 560/173
[58] Field of Search .................. 560/38, 170, 40, 153, 560/155, 168, 169, 171, 173; 260/465.4; 546/335; 548/344, 491, 532, 535

[56] References Cited

FOREIGN PATENT DOCUMENTS 730599  5/1955  United Kingdom .

OTHER PUBLICATIONS

Erlanger et al, *J. Am. Chem. Soc.*, vol. 73, pp. 3508–3510, (1951).
Rudinger et al, *Coll. Czech. Chem. Comm.*, vol. 23, pp. 1947–1957, (1958).
Wilchek et al, *J. Org. Chem.*, vol. 28, pp. 1874–1875, (1963).
Brenner et al, *Chemical Abstracts*, vol. 51, No. 4278a, (1957).
Greenstein et al, *Chemistry of the Amino Acids*, reprinted ed., Robt. E. Krieger Pub. Co., Malabar, Florida, pp. 860–876, 1278–1281, (1984).
Bodanszky, *Principals of Peptide Synthesis*, Springer-Verlag, Berlin, pp. 24–26, (1984).
Fieser et al, *Reagents for Organic Synthesis*, vol. 1, pp. 856, 858–859, (1967).
Iwakura et al, "Benzyl Esters of α-Amino Acids", *Bulletin of the Chemical Society of Japan*, vol. 37, pp. 1707–1709 (1964).
Matzner et al, "The Chemistry of Chloroformates", *Chemical Reviews*, vol. 64, pp. 654–655 and 677–684 (1964).
Domagala, "A Mild, Rapid, and Convenient Esterification of α-Keto Acids", *Tetrahedron Letters*, vol. 21, pp. 4997–5000 (1980).
Kim et al, "A New Convenient Method for the Esterification of Carboxylic Acids", *Tetrahedron Letters*, vol. 24, No. 32, pp. 3365–3368 (1983).

*Primary Examiner*—Natalie Trousof
*Assistant Examiner*—Bruce D. Gray
*Attorney, Agent, or Firm*—George D. Morris

[57] ABSTRACT

Amino acid ester hydrohalide is produced by reacting amino acid, alcohol, and halocarbonyl compound represented by the formula:

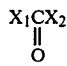

in the presence of an excess of the alcohol and under substantially anhydrous conditions, wherein $X_1$ and $X_2$ are each independently fluoro, chloro, bromo, trichloromethoxy or tribromomethoxy.

18 Claims, No Drawings

METHOD FOR PREPARING AMINO ACID ESTER HYDROHALIDES

BACKGROUND OF THE INVENTION

Ester hydrohalides of amino acids are often employed as raw materials in the preparation, by a sequence of reactions, of compounds having various uses. Many of them, as for example, L-threonine methyl ester hydrochloride, and L-serine methyl ester hydrochloride, may be used in the preparation of monocyclic β-lactam antibiotics, commonly known as monobactams. L-Phenylalanine methyl ester hydrochloride, may be used in the preparation of aspartame, which is a low-calorie sweetener.

The traditional method for preparing ester hydrochlorides of amino acids is by esterifying the amino acid using alcoholic hydrogen chloride solution. This procedure is cumbersome and lengthy, involving several solvent stripping operations to remove all water and to drive the reaction to completion. Thus, two days are frequently required for a laboratory-sized batch.

A faster known method taking about three hours for a laboratory-sized batch involves the use of thionyl chloride, an expensive raw material, and one that results in the release of sulfur dioxide which presents disposal problems. In many cases, the reaction of thionyl chloride and an amino acid results in a product which, after isolation from the reaction mixture, is a highly viscous liquid which is difficult to crystallize. Although it is not desired to be bound by any theory, it is believed that trace amounts of impurities retard the crystallization.

A third method known for preparing ester hydrochlorides of α-amino acids involves phosgenation of α-amino acids to form N-carboxyanhydrides (otherwise known as N-carbonoanhydrides or NCA's) and subsequent reaction of the N-carboxyanhydrides with alcohols. See for example, Iwakura et al, "Benzyl Esters of αn-Amino Acids", Bulletin of the Chemical Society of Japan, Volume 37, pages 1707–1709 (1964).

It is also known that esters of carboxylic acids may be prepared by reacting the acids with the appropriate chloroformates. See for example, British Patent Specification 730,599 (1955); Matzner et al, "The Chemistry of Chloroformates", Chemical Reviews, Volume 64, pages 654–655 and 677–684 (1964); Domagala, "A Mild, Rapid, and Convenient Esterifiction of α-Keto Acids", Tetrahedron Letters, Volume 21, pages 4997–5000 (1980); Kim et al, "A New Convenient Method for the Esterification of Carboxylic Acids", Tetrahedron Letters, Volume 24, No. 32, pages 3365–3368 (1983). Chloroformates, however, are not inexpensive materials. The preparation of chloroformates as end products suitable for commerce usually includes one or more purification steps such as a stripping step for the removal of excess phosgene. In some cases the chloroformates are distilled in order to separate them from the carbonates formed as by-products. Each of these additional steps adds to the cost of producing the chloroformates.

THE INVENTION

A method has now been found for preparing ester hydrohalides of amino acids in which the rate of reaction is rapid as compared with the hydrogen chloride method, which does not employ thionyl chloride, and which does not require separate preparation of the haloformate. Accordingly, the present invention is a method comprising reacting amino acid, alcohol, and halocarbonyl compound represented by the formula:

$$\underset{\underset{O}{\|}}{X_1 C X_2} \qquad (I)$$

in the presence of an excess of the alcohol with respect to the amino acid, and under substantially anhydrous conditions, to produce ester hydrohalide of the amino acid and the alcohol, wherein $X_1$ and $X_2$ are each independently fluoro, chloro, bromo, trichloromethoxy, or tribromomethoxy.

The amino acids used as reactants in the present invention are widely varied. They may be polypeptides of one, two, three, four, five, or more fundamental amino acid units. More usually, however, they are the fundamental amino acids themselves. Examples include alanine, valine, leucine, isoleucine, proline, phenylalanine, tryptophan, methionine, glycine, serine, threonine, tyrosine, asparagine, glutamine, aspartic acid, glutamic acid, lysine, arginine, histidine, 4-hydroxyproline, 5-hydroxylysine, ⊖-N-methyllysine, 3-methylhistidine, desmosine, isodesmosine, β-alanine, γ-aminobutyric acid, homoserine, citrulline, ornithine, canavanine, djenkolic acid and β-cyanoalanine. The preferred amino acids are serine, threonine, and phenylalanine. It is preferred that the amino acid be free of thiohydroxy and dithio groups.

The amino acids may be of any stereoisomeric form. In the case of amino acids having only one asymmetric carbon atom, they may individually have the L-configuration or the D-configuration, although the L-configuration is more common. Mixtures of amino acids, including racemic mixtures, may also be used.

The alcohols employed in the process may be widely varied. In general, they are liquid at the reaction temperature. Of the alcohols, benzyl alcohol or alkanol, which may be straight chain or branched, containing from 1 to about 8 carbon atoms is most often used. In many cases the alkanol contains from 1 to about 4 carbon atoms. Methanol is preferred. Only one alcohol or a mixture of different alcohols may be employed as desired.

Examples of halocarbonyl compounds within Formula I include phosgene, bromophosgene, fluorophosgene, fluorochlorophosgene, bromochlorophosgene, trichloromethyl chloroformate, tribromomethyl bromoformate, and bis(trichloromethyl) carbonate. Phosgene is preferred. Only one halocarbonyl compound or a mixture of different halocarbonyl compounds may be used.

The relative amounts of alcohol and amino acid present may vary widely, but in general the alcohol is in excess, and preferably it is in substantial excess. Often the equivalent ratio is in the range of from about 3:1 to about 100:1. From about 20:1 to about 50:1 is preferred.

The relative amounts of halocarbonyl compound and amino acid introduced to the reaction may also vary widely, but usually the halocarbonyl compound is in excess. In most cases the equivalent ratio of halocarbonyl compound to amino acid introduced to the reaction is at least about 1:1. Often the equivalent ratio is in the range of from about 2:1 to about 10:1. From about 3:1 to about 6:1 is preferred. In determining the equivalent ratio of halocarbonyl compound to amino acid introduced to the reaction, the equivalency of the halocarbonyl compound is taken on the basis of carbonyl dihalide functionality. Such equivalency, expressed in terms of equivalents per mole, is the value of n in the following empirical formula of the halocarbonyl compound and mixtures thereof:

$$[CO(Halogen)_2]_n \quad (II)$$

For individual halocarbonyl compounds, the value of n is 1, 2, or 3, whereas for mixtures of halocarbonyl compounds the average value of n will be an integer or fractional number in the range of from 1 to 3. As examples, for phosgene there is one equivalent per mole; for trichloromethyl chloroformate there are two equivalents per mole; and for bis(trichloromethyl) carbonate, there are three equivalents per mole.

The reaction is believed to be a liquid phase reaction, although one or more solid phases are sometimes present. It may be conducted batchwise, continuously, semi-batchwise, or semi-continuously.

The temperatures at which the reaction may be conducted may vary considerably, but usually they are in the range of from about $-10°$ C. to about $+75°$ C. Temperatures in the range of from about $+20°$ C. to about $+60°$ C. are preferred.

The reaction is ordinarily conducted at or near ambient atmospheric pressure, although greater or lesser pressures may be used when desired.

The reaction may be conducted in the presence of one or more extrinsic inert solvents, but it is preferred that the reaction be neat, that is, that the reaction be conducted in the substantial absence of extrinsic inert solvent.

The ester hydrohalide of the amino acid may be separated from the reaction mixture by conventional procedures such as stripping, precipitation, decantation, filtration, centrifugation, and drying.

The invention is further described in conjunction with the following example which is to be considered illustrative rather than limiting, and in which all parts are parts by weight and all percentages are percentages by weight unless otherwise specified.

EXAMPLE

A 1-liter, 4-necked flask equipped with a mechanical agitator, a thermometer, a gas-inlet tube, a vertical condenser cooled by a mixture of solid carbon dioxide and isopropanol, and a gas bubble tube mounted on the outlet of the condenser was charged with 21.0 grams (0.200 mole) of L-serine and 237.3 grams (7.41 moles) of methanol. The flask was placed in a solid carbon dioxide and isopropanol cooling bath. The reaction mixture was cooled to $-11°$ C. and phosgene was added below the surface of the liquid via the gas-inlet tube according to the schedule of Table 1.

TABLE 1

| Time hours: minutes | Temperature, °C. | Phosgene Added, grams, cumulative | Remarks |
|---|---|---|---|
| 0:00 | −11 | 0 | Solids present. Phosgene addition begun. |
| 0:18 | −10 | 25.6 | All solids have dissolved. |
| 0:40 | −12 | 48.7 | |
| 0:49 | −11 | 61.6 | Addition of phosgene discontinued. |
| 1:50 | −7 | 61.6 | Replaced cooling bath with a warm water bath. |

TABLE 1-continued

| Time hours: minutes | Temperature, °C. | Phosgene Added, grams, cumulative | Remarks |
|---|---|---|---|
| 2:15 | +37 | 61.6 | A steady evolution of gas was observed. |

The reaction mixture was then stirred at about 40° C. for a further 17 hours while additional samples were taken periodically. Thin layer chromatographic analyses of the samples showed that the amounts of L-serine methyl ester hydrochloride, and L-serine present in the reaction mixture remained essentially constant after stirring for about 4 hours at about 40° C. The spots on the chromatographic plates representing the methyl ester hydrochloride product were much larger than those representing L-serine, but the presence of the latter indicated that not all of the L-serine had been converted.

The reaction mixture was cooled to $-8°$ C. using a solid carbon dioxide- isopropanol cooling bath and additional phosgene was introduced according to the schedule of Table 2.

TABLE 2

| Time hours: minutes | Temperature, °C. | Phosgene Added, grams, cumulative | Remarks |
|---|---|---|---|
| 0:00 | −8 | 61.6 | Phosgene addition begun. |
| 0:23 | −10 | 82.9 | Addition of phosgene discontinued. Replaced cooling bath with a warm water bath. |
| 0:40 | +38 | 82.9 | Some gas evolution. |

The reaction mixture was stirred for an additional 2 hours at about 40° C. Thin layer chromatographic analysis of the reaction mixture showed it to be essentially the same as before the last 21.3 grams of phosgene had been added.

With further stirring, the condenser was replaced by a distillation head and the gas-inlet tube was replaced by a stopper. A heating mantle was applied and with gentle heating (about 50° C.) and under the vacuum applied using a water aspirator (absolute pressure as low as about 2.7 kilopascals), the solution was distilled until a very concentrated slurry remained. The vacuum was broken and about 100 cubic centimeters of carbon tetrachloride was added. The slurry was then filtered. The filter cake was washed with 50 cubic centimeters of fresh carbon tetrachloride. Most of the liquid was removed by pulling air through the filter cake using the vacuum applied by a water aspirator. The filter cake was then dried overnight in a convection oven at about 50° C. Thin layer chromatograph analysis showed the dried solids to contain L-serine methyl ester hydrochloride, and a small amount of L-serine. The dried solids were dissolved in about 50 cubic centimeters of methanol and about 100 cubic centimeters of carbon tetrachloride was added to induce crystallization. The mixture was chilled in an ice bath and filtered. The filter cake was dried as above. The resulting product melted in the range of from 162° C. to 165° C. and weighed 24.5 grams, representing a yield of 78.8 percent, based on L-serine. Thin layer chromatography showed no L-serine to be present. Infrared and nuclear magnetic resonance spectra of the product matched the standard spectra of L-serine methyl ester hydrochloride.

This example shows that the reaction of L-serine to L-serine methyl ester hydrochloride was essentially completed after heating the reaction mixture at 40° C. for about 4 hours. It is expected that a higher temperature at the beginning of phosgene addition will increase the rate of reaction.

Although the present invention has been described with reference to specific details of certain embodiments thereof, it is not intended that such details should be regarded as limitations upon the scope of the invention except insofar as they are included in the accompanying claims.

I claim:

1. A method comprising reacting amino acid, alcohol, and halocarbonyl compound represented by the formula:

in the presence of an excess of said alcohol with respect to said amino acid, and under substantially anhydrous conditions, to produce ester hydrohalide of said amino acid and said alcohol, wherein $X_1$ and $X_2$ are each independently fluoro, chloro, bromo, trichloromethoxy, or tribromomethoxy.

2. The method of claim 1 wherein the equivalent ratio of said alcohol to said amino acid introduced to the reaction is in the range of from about 3:1 to about 100:1

3. The method of claim 1 wherein the equivalent ratio of said halocarbonyl compound to said amino acid introduced to the reaction is at least about 1:1.

4. The method of claim 1 wherein the equivalent ratio of said halocarbonyl compound to said amino acid introduced to the reaction is in the range of from about 2:1 to about 10:1.

5. The method of claim 1 wherein the reaction is conducted at temperatures in the range of from about −10° C. to about +75° C.

6. The method of claim 1 wherein said alcohol is benzyl alcohol or straight chain or branched alkanol containing from 1 to about 8 carbon atoms.

7. The method of claim 1 wherein said alcohol is methanol.

8. The method of claim 1 wherein said halocarbonyl compound is phosgene.

9. A method comprising reacting:
(a) amino acid selected from the group consisting of serine, threonine, and phenylalanine,
(b) alcohol selected from the group consisting of benzyl alcohol and straight chain or branched alkanol containing from 1 to about 8 carbon atoms, and
(c) phosgene, in the presence of an excess of said alcohol with respect to said amino acid, and under substantially anhydrous conditions, to produce ester hydrochloride of said amino acid and said alcohol.

10. The method of claim 9 wherein said alcohol is methanol.

11. The method of claim 9 wherein:
(a) the equivalent ratio of said alcohol to said amino acid introduced to the reaction is in the range of from about 3:1 to about 100:1;
(b) the equivalent ratio of said phosgene to said amino acid introduced to the reaction is in the range of from about 2:1 to about 10:1; and
(c) the reaction is conducted at temperatures in the range of from about −10° C. to about +75° C.

12. The method of claim 11 wherein said alcohol is methanol.

13. The method of claim 7 wherein said amino acid is serine.

14. The method of claim 9 wherein said amino acid is threonine.

15. The method of claim 9 wherein said amino acid is phenylalanine.

16. The method of claim 1 wherein said amino acid is serine.

17. The method of claim 1 wherein said amino acid is threonine.

18. The method of claim 1 wherein said amino acid is phenylalanine.